US008819926B2

(12) United States Patent
Yazdanpanah et al.

(10) Patent No.: US 8,819,926 B2
(45) Date of Patent: Sep. 2, 2014

(54) METHODS AND APPARATUSES OF USING METAL NEEDLE ARRAYS FOR SPECIMEN LIFT-OUT AND CIRCUIT EDIT

(76) Inventors: Mehdi M Yazdanpanah, Louisville, KY (US); Romaneh Jalilian, Louisville, KY (US)

( * ) Notice: Subject to any disclaimer, the term of this patent is extended or adjusted under 35 U.S.C. 154(b) by 120 days.

(21) Appl. No.: 13/366,316

(22) Filed: Feb. 4, 2012

(65) Prior Publication Data

US 2013/0199034 A1    Aug. 8, 2013

(51) Int. Cl.
*H01R 43/00* (2006.01)
(52) U.S. Cl.
USPC .... 29/825; 29/402.01; 29/402.03; 29/402.06; 29/402.08
(58) Field of Classification Search
USPC ............... 29/402.01, 402.03, 402.06, 402.08, 29/402.09, 825
See application file for complete search history.

(56) References Cited

U.S. PATENT DOCUMENTS 6,265,235 B1 *   7/2001   McIntosh et al. ............... 438/16

* cited by examiner

*Primary Examiner* — Carl Arbes

(57) ABSTRACT

Embodiments of the present invention provide method and apparatus of restoring probes attached to the manipulator in a control environment (e.g. vacuum chamber of an focus ion beam) without a need to open the vacuum chamber. Another embodiment of the present invention teaches construction and application of various shapes of nanoforks from a nanoneedles array inside a FIB vacuum chamber. In another embodiment, the present invention teaches edition and correction of completed and oxide-coated circuit boards by re-nano-wiring using nanoneedles of a nanoneedles array (as nanowire supply), contained in the same controlled space. In this embodiment, individual nanoneedles in a nanoneedle array are manipulated by a manipulator and placed in such a way to make electrical contact between the desired points.

3 Claims, 23 Drawing Sheets

(b)

(b)

METHODS AND APPARATUSES OF USING METAL NEEDLE ARRAYS FOR SPECIMEN LIFT-OUT AND CIRCUIT EDIT

STATEMENT OF GOVERNMENT INTEREST

This invention was made with Government support under Grant # IIP-1058576 awarded by National Science Foundation, Grant #KSTC184-512-10-107 awarded by Kentucky Science Technology Corporation, and by the National Science Foundation under Grant # IIP-1059286 to the American Society for Engineering Education (ASEE). The government has certain rights in the invention.

BACKGROUND OF THE INVENTION

The microprocessor industry continues to scale down the feature sizes and the number of transistors on VLSI circuits. Scaling below the 100 nm node has produced the situation in which SEM inspection no longer offers suitable resolution to image key artifacts and structures. Therefore, the transmission electron microscope (TEM) is considered to be the method of choice for process control and failure analysis, especially for measurements such as the thickness of non-planar barrier and seed layers. However TEM samples must be thin in order for the high energy electrons to transmit through the samples and image the sample. To prepare such specimens, focused ion beam (FIB) microscope is used to cut a biopsy specimen from the silicon wafer and thin it to be used for TEM imaging and evaluation. After the specimen is cut by FIB, a nanomanipulator is used for "in-situ lift-out" to lift the specimens and put it on the TEM grid for imaging. For that, a sharp probe (mainly a tungsten probe) is brought in contact with the specimen using a nanomanipulator arm. Then, using ion-beam metal deposition, the tungsten probe is welded to the specimen, and the specimen lift and move by the manipulator and placed on the TEM grid. Then, using the FIB, the tungsten probe is cut and separated from the specimen.

However, after each cut, the probe tip become thicker (due to conical shape of the tungsten probe), and finally the user must either sharpen it using the FIB or eventually change the probe when sharpening takes very long time.

As just another challenge in failure analysis of devices in semiconductor industry, currently there are methods for modifying circuits after they are insulated by oxide coatings or similar materials. The circuit can be edited and/or redesigned by forming secondary connections on top of the insulating layer. Currently the FIB is used to first open vias (i.e. hole) in the silicon oxide layer and reach to the metal contact underneath. Then, metal (e.g. tungsten) is deposited using ion-beam metal deposition to fill the vias with metal. Finally the metal is deposited between the two vias to connect the two points together. However the metal deposition rate between the two vias is usually a slow process and takes several minutes to deposit a few micrometer-long contacts.

SUMMARY OF THE INVENTION

In one embodiment of the present invention, sharp probes attached to the manipulator are restored or modified without a need to open up a controlled space which is usually vacuumed. The method/apparatus for in-situ restoration of probe tips saves considerable time and resources. Another embodiment of the present invention teaches construction and application of a nanofork to handle specimen without the need to weld the specimen to the probe. Yet another embodiment of the present invention teaches edition and correction of completed and oxide-coated circuit boards by re-nano-wiring using nanoneedles on nanoneedle arrays contained in the same controlled space.

BRIEF DESCRIPTION OF THE DRAWINGS

FIGS. 8-10 demonstrate the sequences to make a nanofork by welding multiple needles to the probe tip.

FIG. 11 shows the schematic of lifting a specimen by a nanofork without welding the nanofirk to the specimen.

FIGS. 12-13 show the sequences to make a nanoloop by welding multiple needles to the probe tip.

FIGS. 14, 15 and 16 show the sequences of using a nanoloop to lift a specimen without welding.

FIG. 16 shows the nanoloop lifting the specimen.

FIG. 20A shows the side view of the substrate.

FIG. 20B shows how the needle approaches circuits substrate.

FIG. 20C shows bringing into contact the nanoneedle with the first desired point of contact.

FIG. 20D shows welding for the first desired point of contact.

FIG. 20E shows the cutting of the nanoneedle at the desired location for second contact.

DETAILED DESCRIPTION OF THE PREFERRED EMBODIMENTS

Figure 1A:
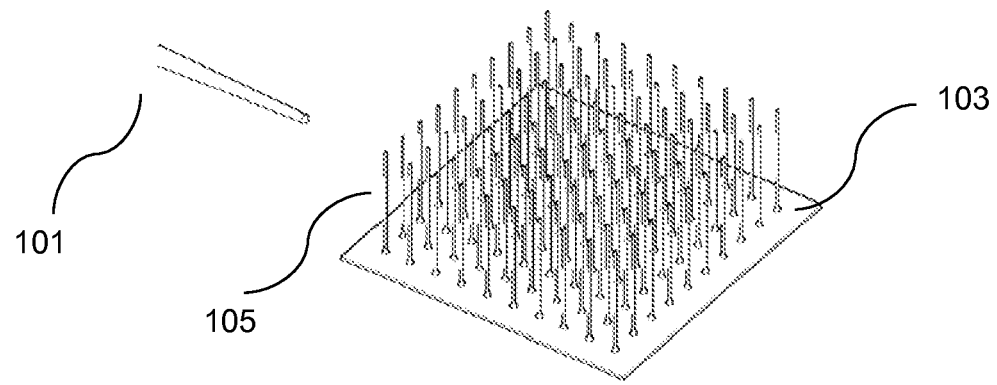
FIG. 1A shows a schematics of a metal needle array and a probe tip (tungsten or similar).
Figure 1B:
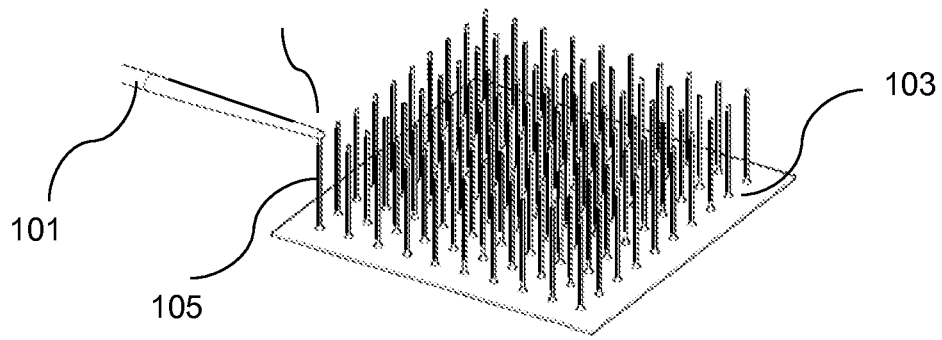
FIG. 1B shows a schematics of a probe tip that is brought in contact and welded to one metal needle in the array to be restored or modified.
Figure 1C:
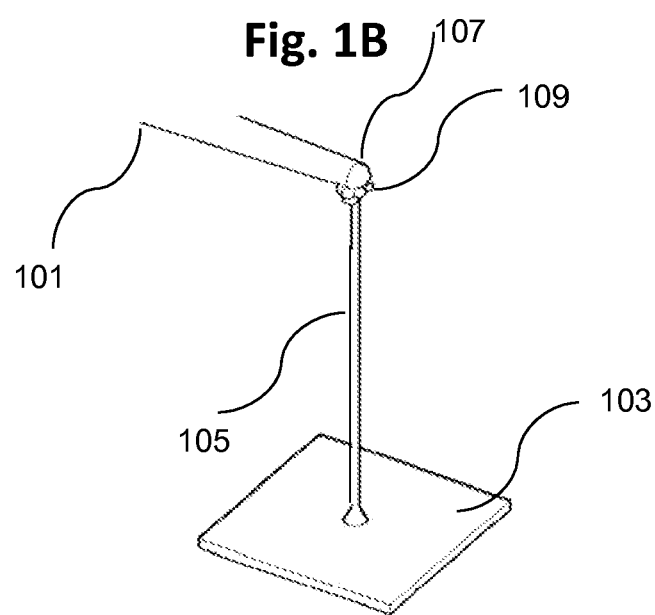
FIG. 1C demonstrates the action showing only one needle.
Figure 2A:
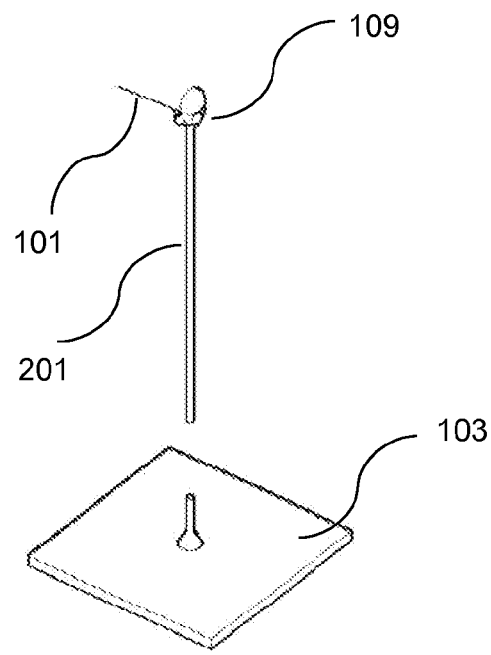
FIG. 2A shows a schematic of a metal needle that is welded to the probe tip.
Figure 2B:
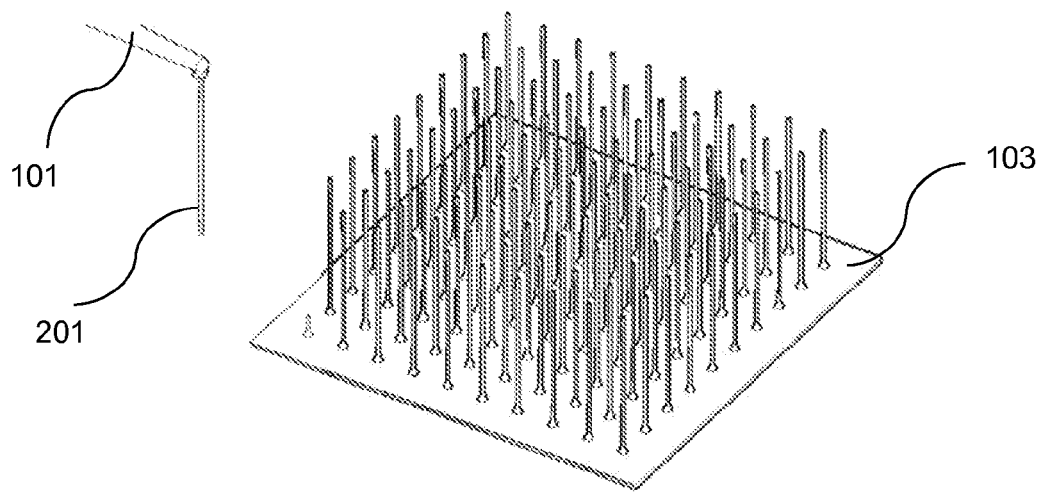
FIG. 2B shows a schematic of a metal needle that is cut from the array substrate to restore a probe tip.
Figure 3A:
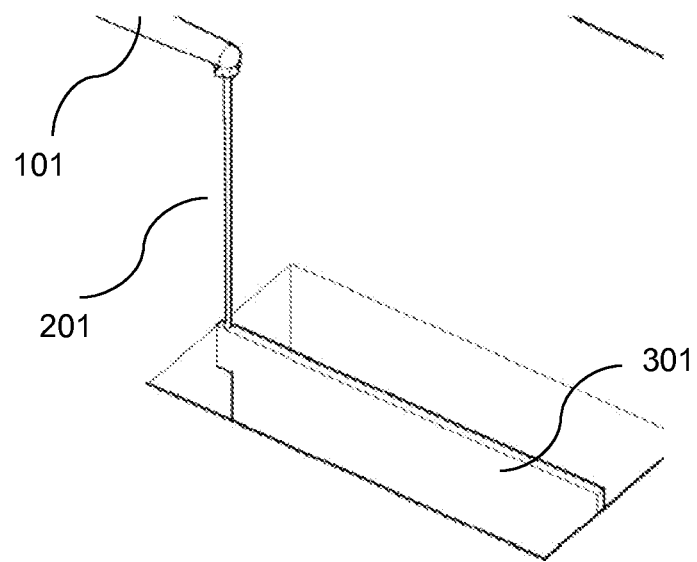
FIG. 3A shows a schematic of the restored probe that is brought in contact with a specimen.
Figure 3B:
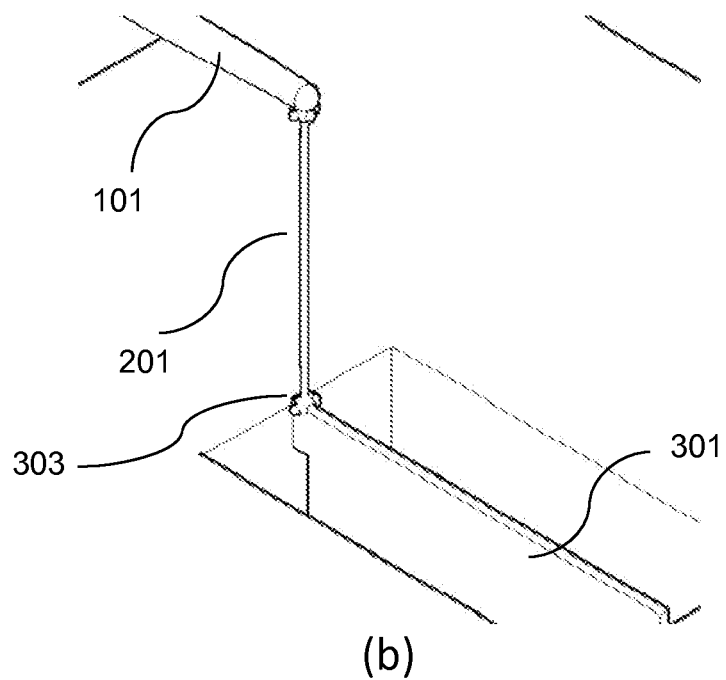
FIG. 3B shows a schematic of the restored probe that is welded to the specimen.
Figure 4A:
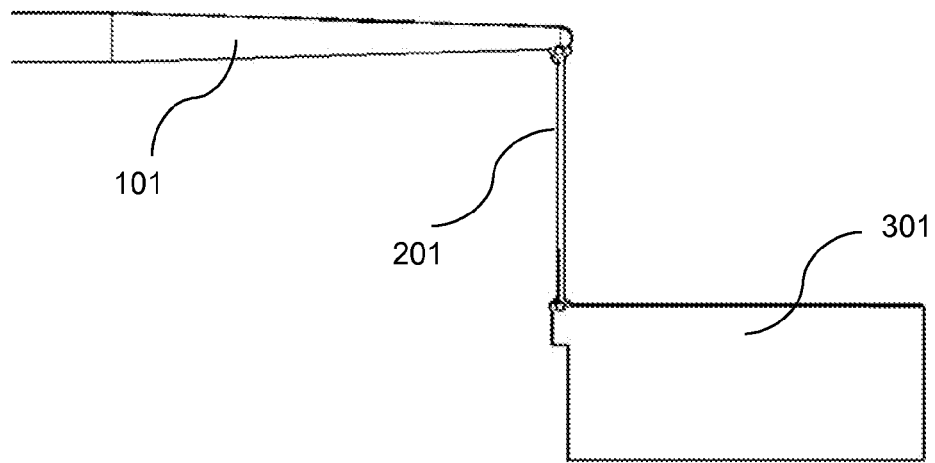
FIG. 4A shows a schematic of the specimen that is lifted by the restored tip.
Figure 4B:
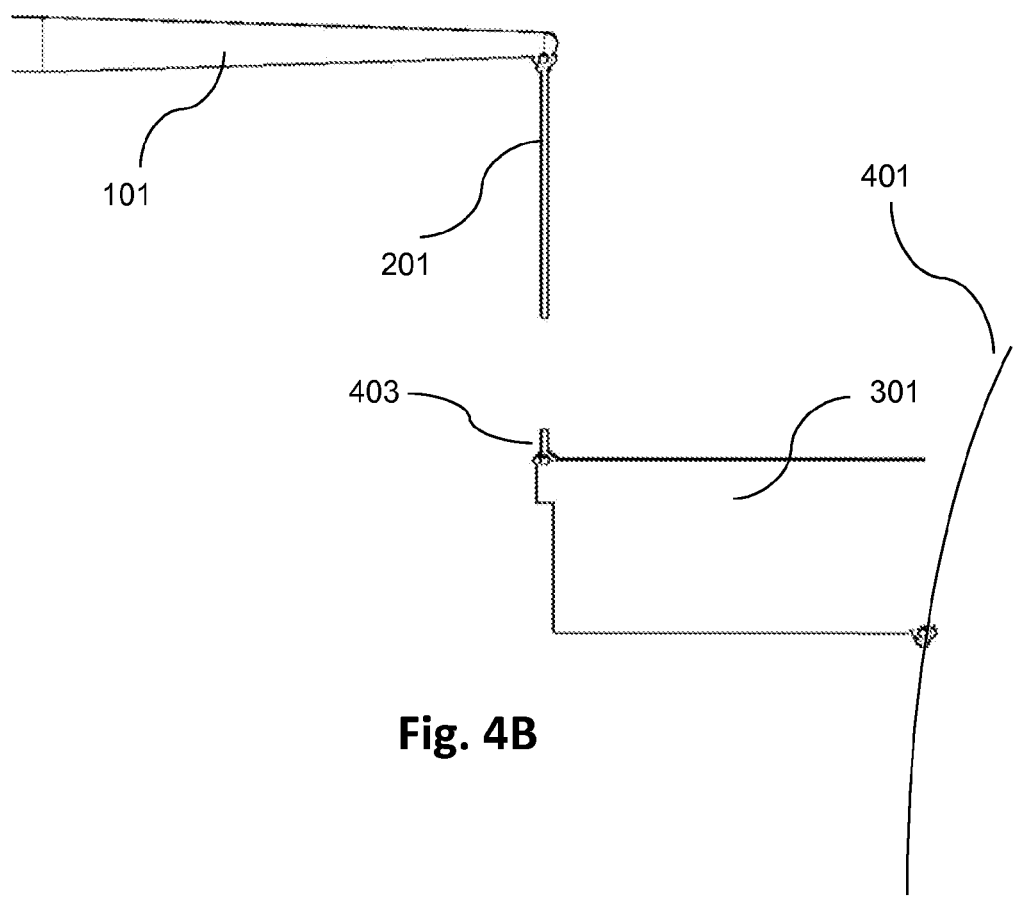
FIG. 4B demonstrates how the needle is cut from the specimen.

One embodiment of the present invention is a method for restoring the probe tip by adding a new tip to the tip of a probe that is blunt or shortened, inside the FIB chamber without breaking the vacuum. This embodiment comprises the steps of loading an array of freestanding needles through the load lock into the FIB chamber, bringing the tungsten probe in contact with one of the needles in the array, welding the needles to the probes by ion-beam metal deposition, cutting the other end of the needle from the array to add the needle from the array to the probe. In one embodiment, this process is repeated whenever the needle is cut or shortened and/or whenever the probe needs to be sharpened again. In this embodiment, having a large inventory of needles in the array inside the closed, vacuumed space, a probe tip can be restored numerous times. In one embodiment, an array of having 1000 needles with a length of 20 to 50 μm long can have a sum of 20 to 50 mm long needle and can last for several thousand lifts.

In one embodiment, the needle array can be coated with a metal coating (such as tungsten) or multiple metal coating to be stable in the FIB. In this mode, by controlling the thickness of the coated metal film, the needles thickness in the array can be controlled to manipulate the electrical, mechanical and chemical properties of the nanoneedles in the array.

FIG. 1-7 show the schematic of the restoring a probe tip. Based on this embodiment, a conical tungsten wire (101) is connected to a micromanipulator (not shown in the drawings), which will allow the wire to be moved in the X, Y, and Z axes with nano-scale resolution. In one embodiment, an array of needles (103) with specific lengths and widths are grown and coated with numerous layers of metals or other materials to manipulate physical properties. In one embodiment, this array of nanoneedles (103), containing up to thousands of nanoneedles (105) is placed within the controlled environment which is usually vacuumed. To transport a specimen, the tungsten wire (101) is first positioned so that the probe tip (107) touches a nanoneedle (105) tip in the array (FIG. 1b). In one embodiment, the probe tip (107) is welded (109) to the tip of the nanoneedle (103), (FIG. 1c) and then the nanoneedle (103) welded to the tungsten wire is severed or otherwise cut from the array (FIG. 2a) forming a nanoneedle tip (201); and finally the tungsten wire/probe (101) with the nanoneedle tip (201) is moved away from the array (FIG. 2b) and positioned next to an array of specimens (not shown here). In one embodiment the nanoneedle probe (201) is then positioned next to a single specimen (301) to be extracted (FIG. 3a). Then the tip of the nanoneedle probe (201) is welded (303) to the specimen (301) (FIG. 3b). In this embodiment, the specimen (301), which is now attached to the nanoneedle probe (201), is cut from the specimen substrate and removed from the specimen array (FIG. 4a) and moved to the target location. As shown in FIG. 4b, once it is in position, the specimen (301) is welded to the target location (401) and then the nanoneedle probe is cut by the ion beam from the specimen and the probe is removed. After the nanoneedle is cut from the specimen (301), a small piece of the nanoneedle (403) remains attached to the specimen (301).

Figure 5A:
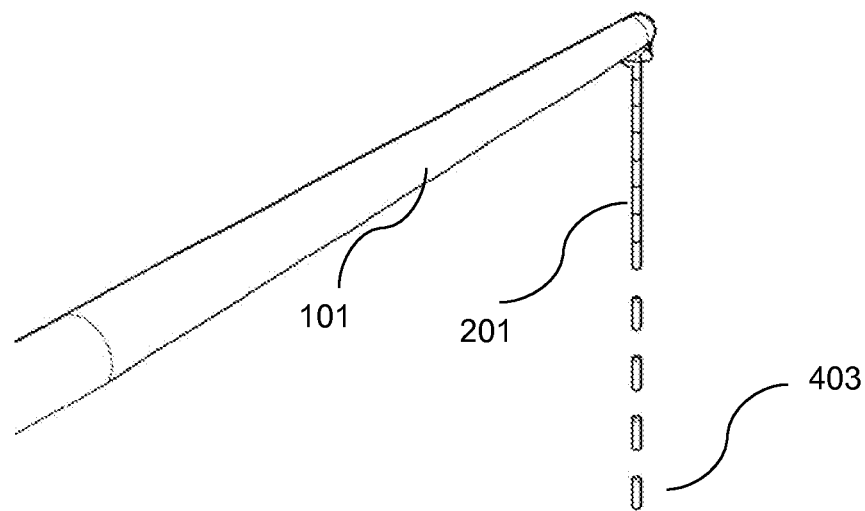
FIG. 5A shows a schematic of the restored probe as the metal needle is getting shorter and shorter after each cut.
Figure 5B:
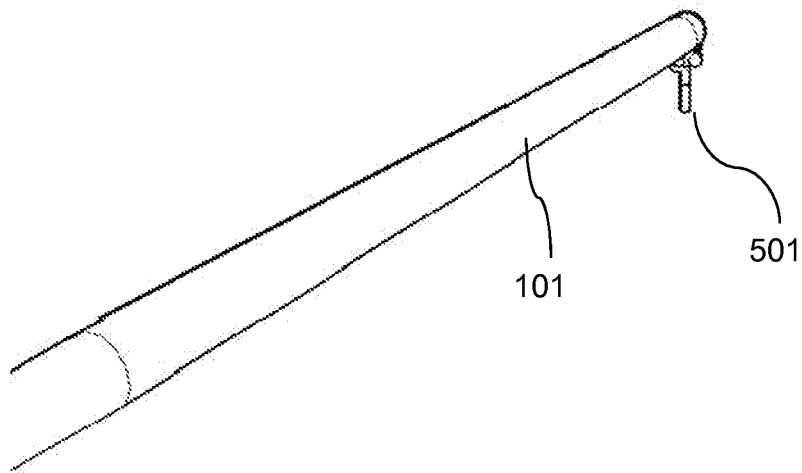
FIG. 5B shows a metal needle which is very small after several use.

Shown in FIG. 5, as pieces of the nanoneedle tip (403) of the probe are severed/cut when removing the specimen, the nanoneedles get shorter and shorter (FIG. 5a) until the nanoneedles is almost consumed entirely (FIG. 5b) and only a small piece (501) remains.

Figure 6A:
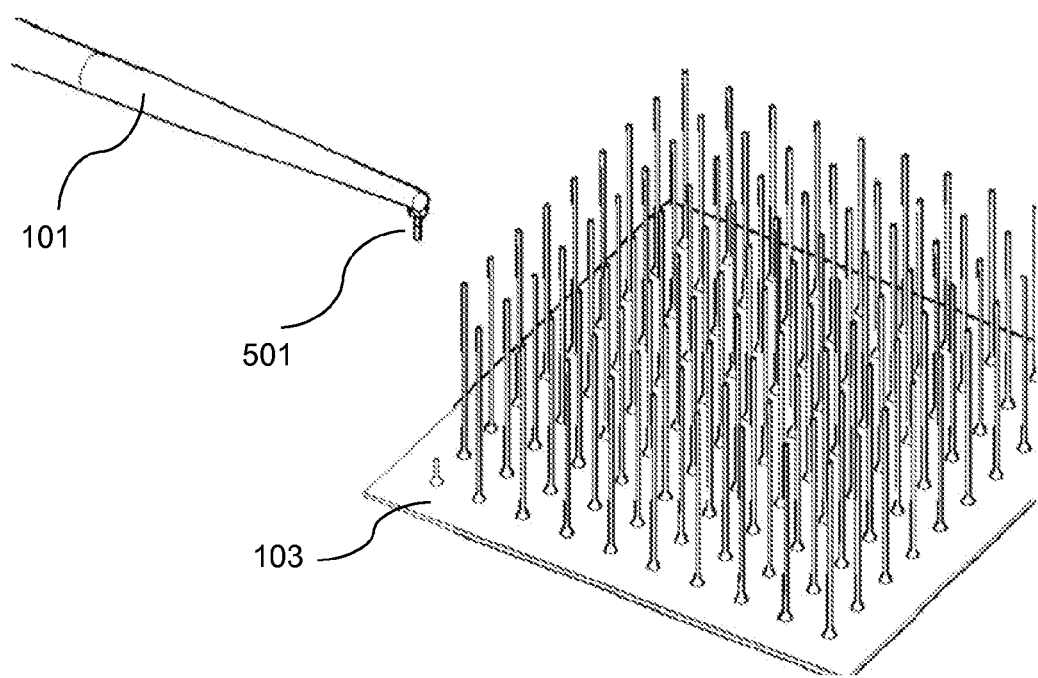
FIG. 6A shows a schematic of the metal needle array and the probe that is brought in contact with the second needle to restore again after diminishing the first needle.
Figure 6B:
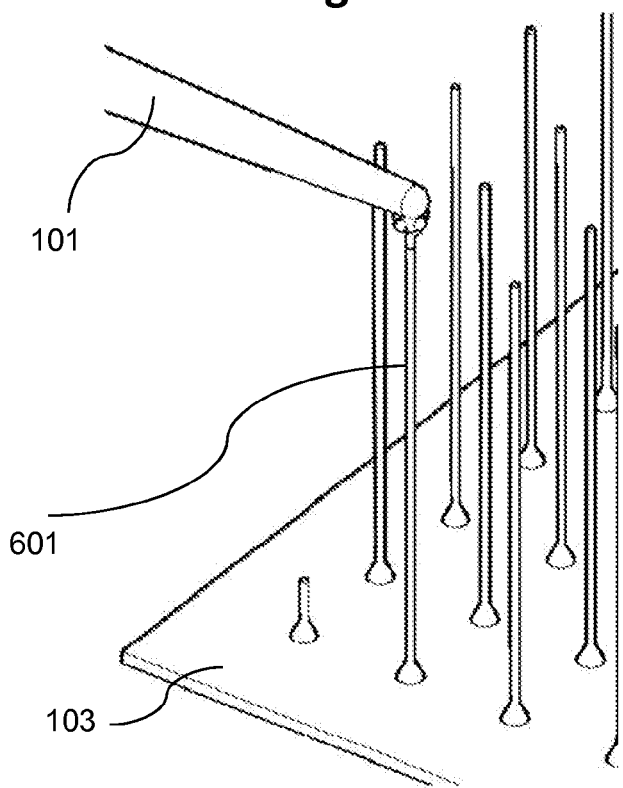
FIG. 6B shows a schematic of the welding of metal needle array and the probe.
Figure 7A:
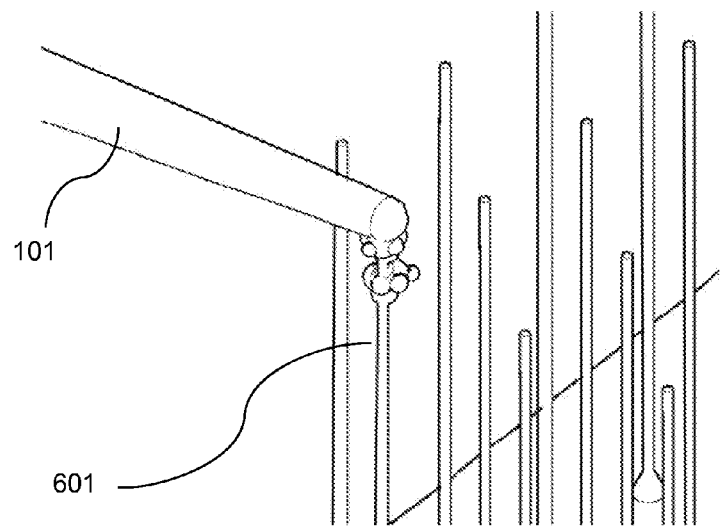
FIG. 7A shows a schematic of the second metal needle that is welded to the probe tip.
Figure 7B:
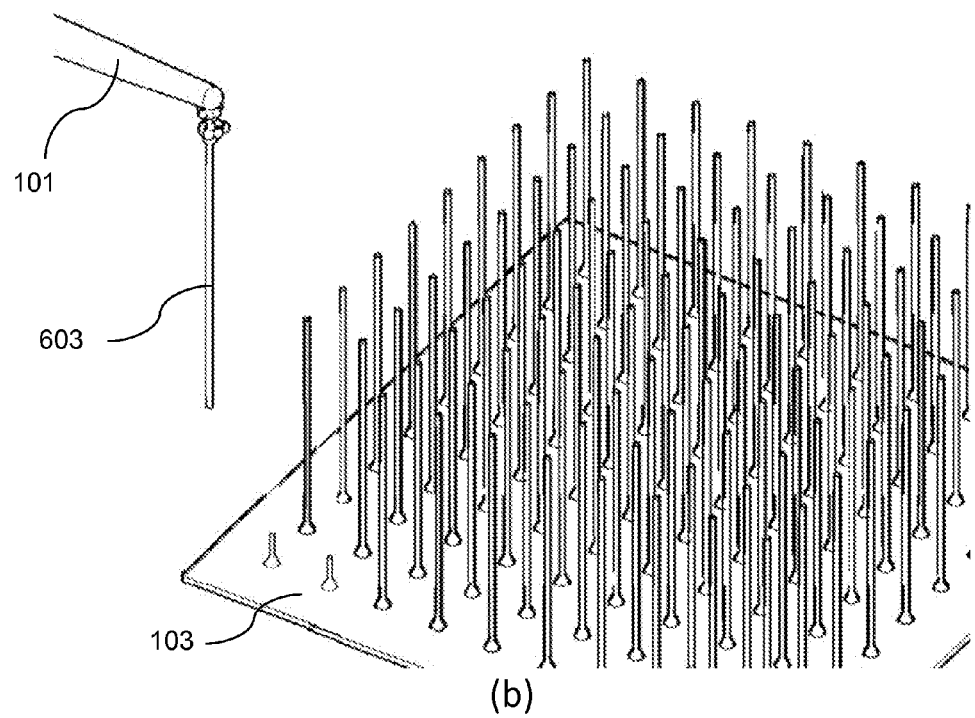
FIG. 7B shows a schematic of the second metal needle that is cut from the array substrate to restore the probe tip for a second time.
Figure 8A:
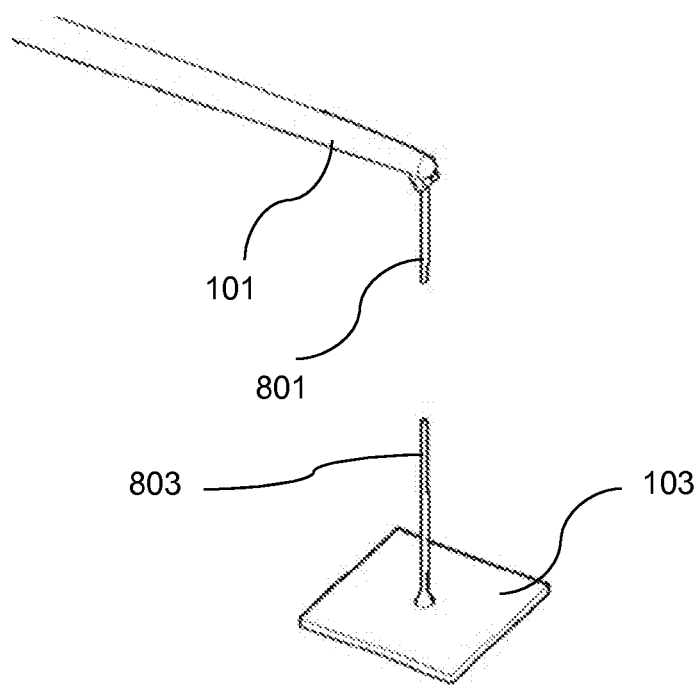
FIG. 8A shows the first needle is cut.
Figure 8B:
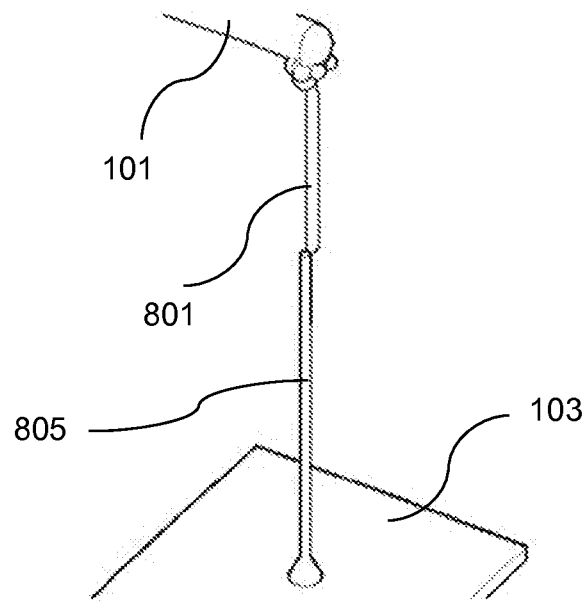
FIG. 8B shows how the needle pieces are brought in contact.
Figure 9A:
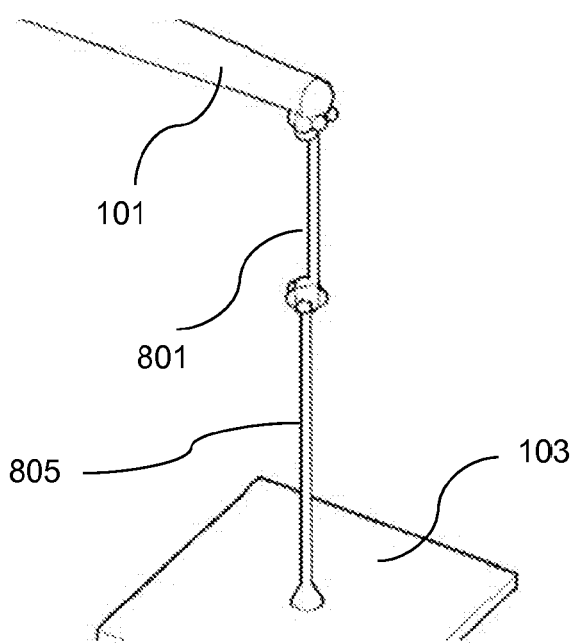
FIG. 9A shows how the needle pieces are welded.
Figure 9B:
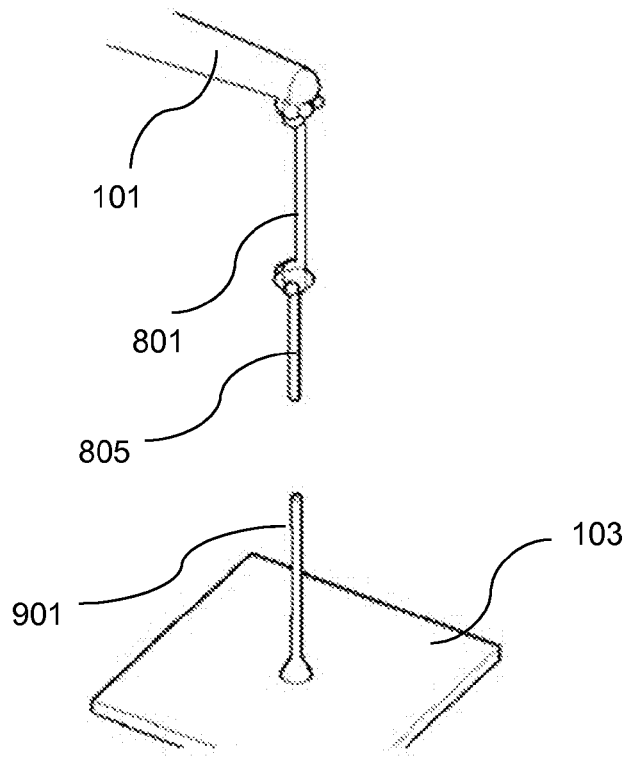
FIG. 9B shows a second needle is cut.
Figure 10A:
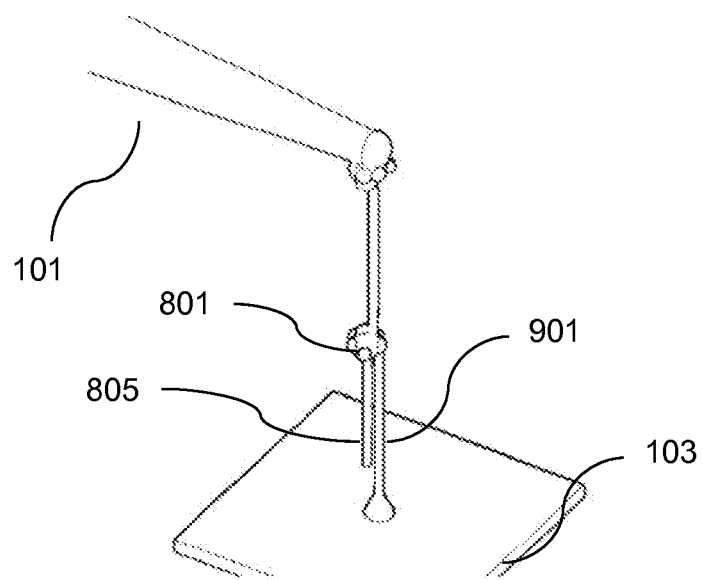
FIG. 10A shows how the needle pieces are brought in contact in the second step.
Figure 10B:
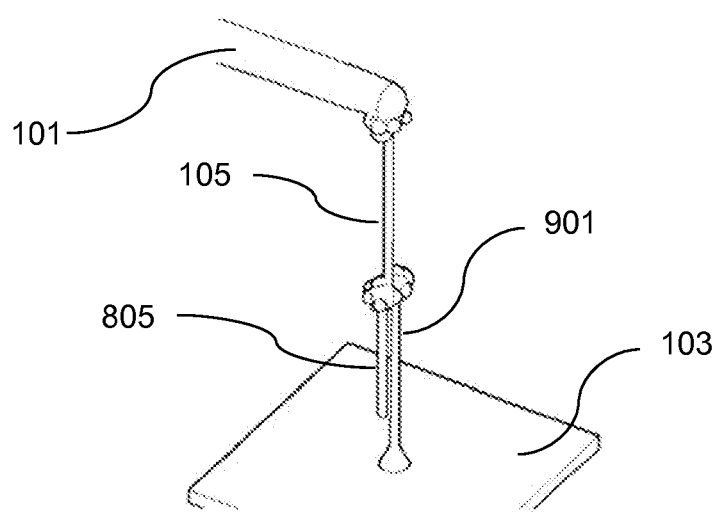
FIG. 10B shows how the needle pieces are welded for the second time.
Figure 10C:
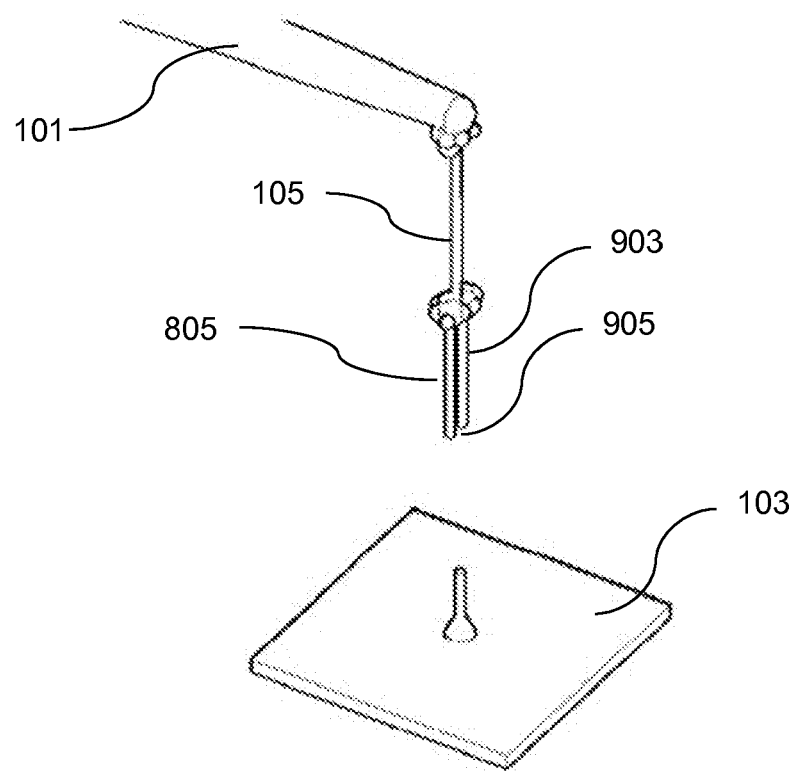
FIG. 10C shows how the needle is cut to form a nanofork.

As shown in FIGS. 6 and 7, in one embodiment of the present invention, the spent nanoneedle tip (501) or the tungsten probe (101) itself (in case there is no residual tip) is brought in contact (FIG. 6a) to the nanoneedle array (103), and touches a new nanoneedle (601) in the nanoneedles array (FIG. 6b). Then the probe tip (101) is welded (FIG. 7a) to the nanoneedles (601), and the nanoneedles (601) is cut from the nanoneedle array (103), hence leaving a new tip (607) in place (FIG. 7b). The "re-sharpened" nanoneedle probe can then be used again. The nanoneedle probe (607) become shorter after each lift and cut and eventually finishes. Therefore the restoring process can be done by adding another needle from the array to the probes (101)

As shown in FIG. 8-11, one embodiment of the present invention represents a method for using a needle array for making special forks for specimen lift-out, without a need for welding the probe tip to the specimen. Depending on the shape of the specimen considered for lift-out, different fork shapes can be fabricated to lift out the specimen without welding the specimen to the probe. One embodiment of the present invention which addresses this objective comprises the steps of, (1) welding one needle (801) to the tungsten probe (101) to form a stem (FIG. 8a), (2) bringing the first needle (801) in contact with a second needle (803) (FIG. 8b), (3) welding the second needle (803) to the first needle (801) at the free end and cut the second needle (803) from the middle to form a first branch (805) as shown in FIGS. 9b, and (4) welding the remaining of the second needle (901) or a third needle (901) to the first needle, at the junction of the first (801) and first branch (805), forming a second branch (903) such that the second branch (903) is parallel to the first branch (805) and therefore forming a nanoscale fork (nanofork) with two arms as shown in FIG. 10c. In this embodiment, there is a small gap (905) between the first (805) and second (903) branch.

Figure 11A:
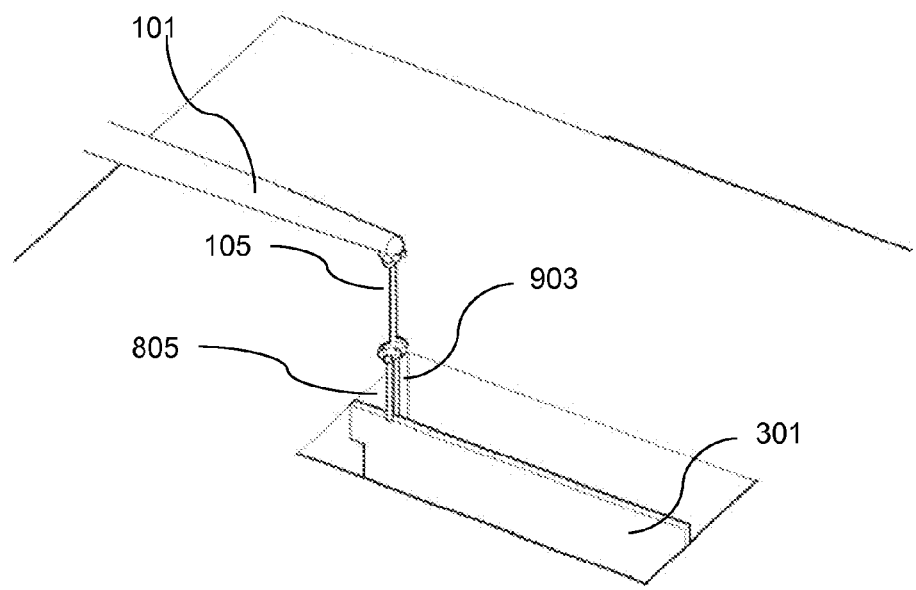
FIG. 11A shows a specimen sliding in the nanofork.
Figure 11B:
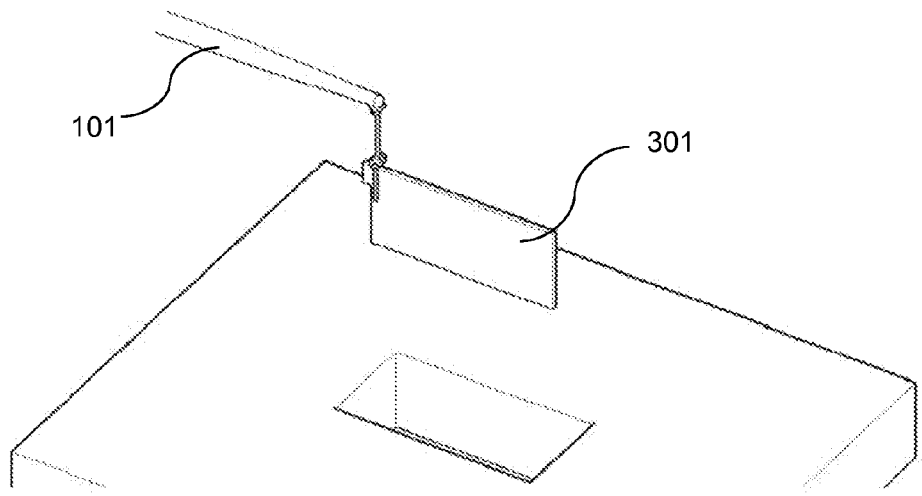
FIG. 11B shows a specimen lifted by the nanofork.

As shown in FIG. 11, in one embodiment, by aligning said fork's opening gap (905) with the specimen (301) such that by pushing the nanofork on the specimen (301), the nanofork's flexible and highly elastic arms (805) and (903) are slightly opened and the specimen (301) slides into being held by above mentioned arms (FIG. 11a). Then, the specimen (301) is cut-off from its base and is lifted by the nanofork (FIG. 11b). In one embodiment, to release the specimen, it is first brought in contact with the TEM grid holder (401) and is welded to the holder, and then the fork is moved away from the specimen to leave the specimen in the TEM grid (401).

Figure 12A:
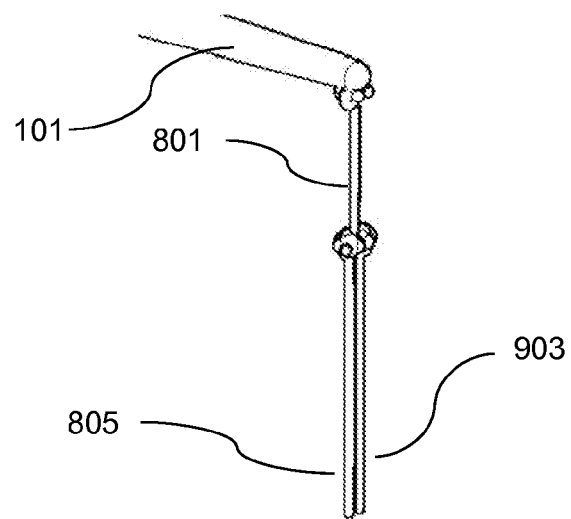
FIG. 12A shows the nanoneedles to form a nanoloop.
Figure 12B:
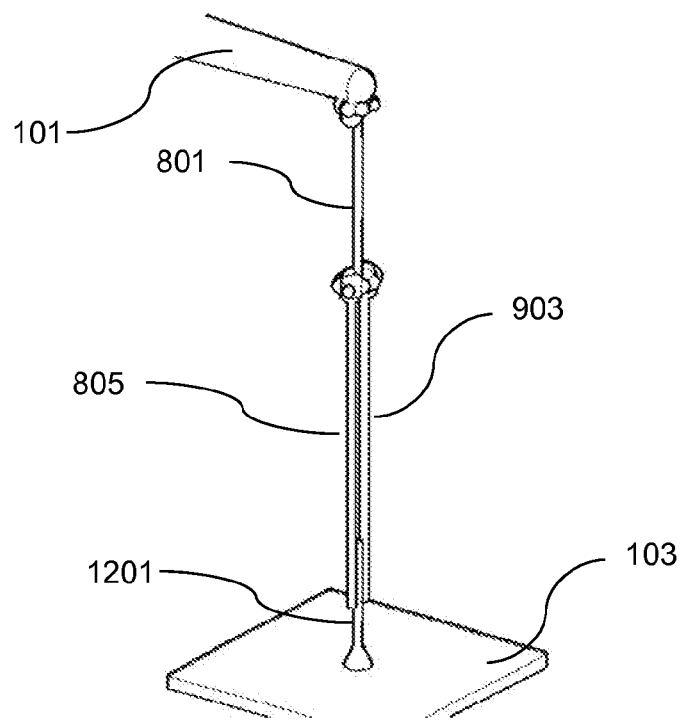
FIG. 12B shows the position of the nanoneedles to form a nanoloop.
Figure 13A:
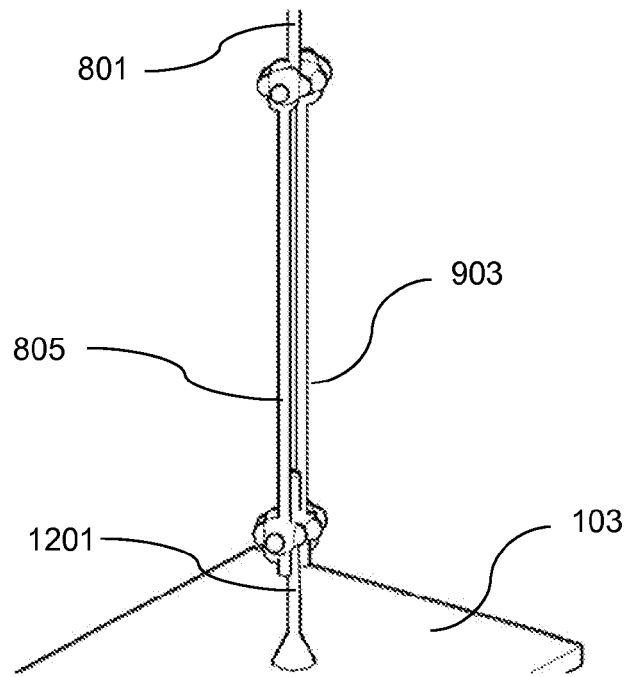
FIG. 13A shows the welding of the nanoneedles to form a nanoloop.
Figure 13B:
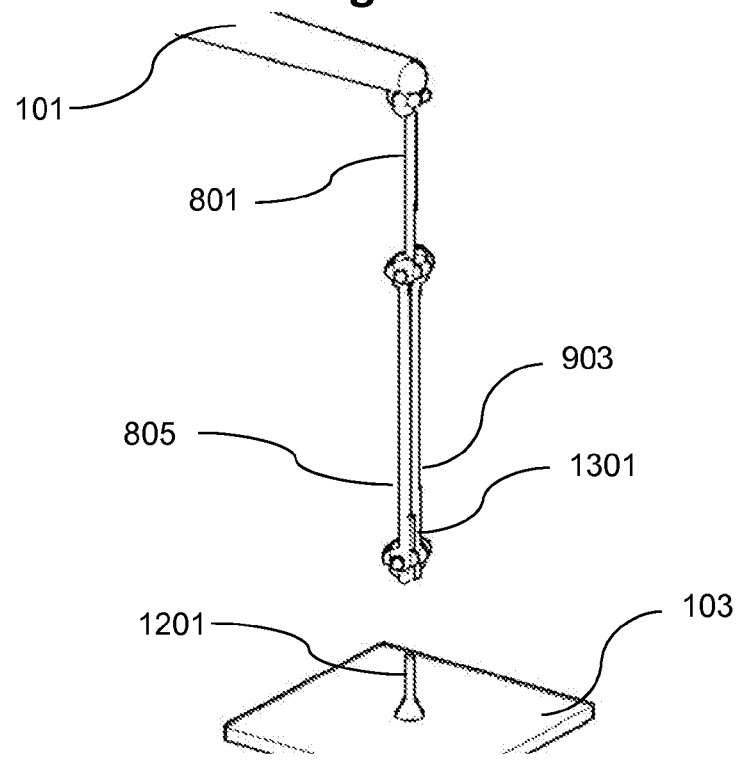
FIG. 13B shows the cutting and final step to form a nanoloop.
Figure 14A:
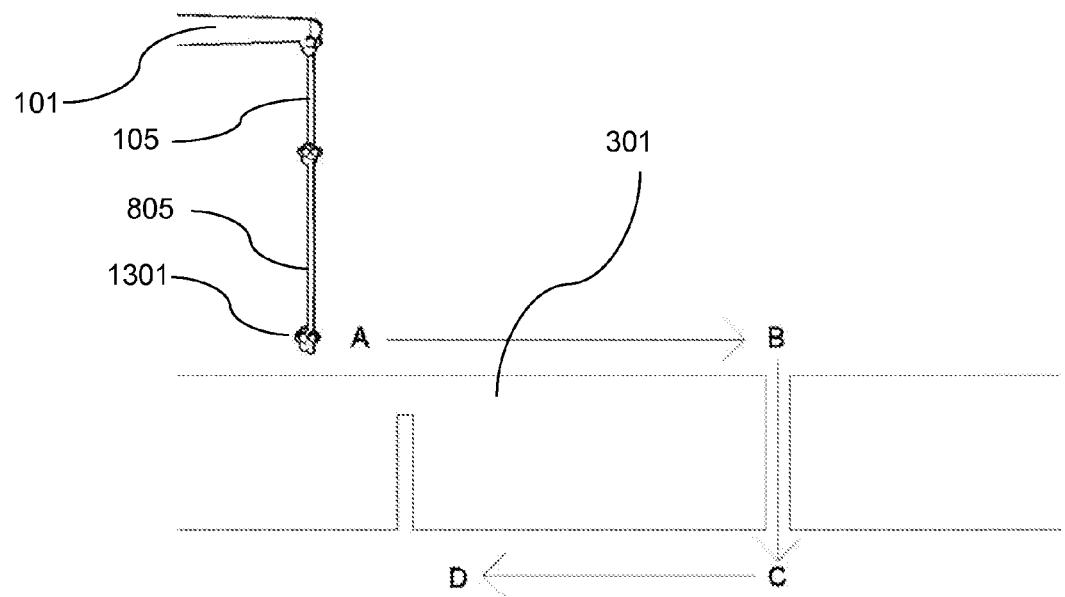
FIG. 14A shows the path the nanoloop needs to travel.
Figure 14B:
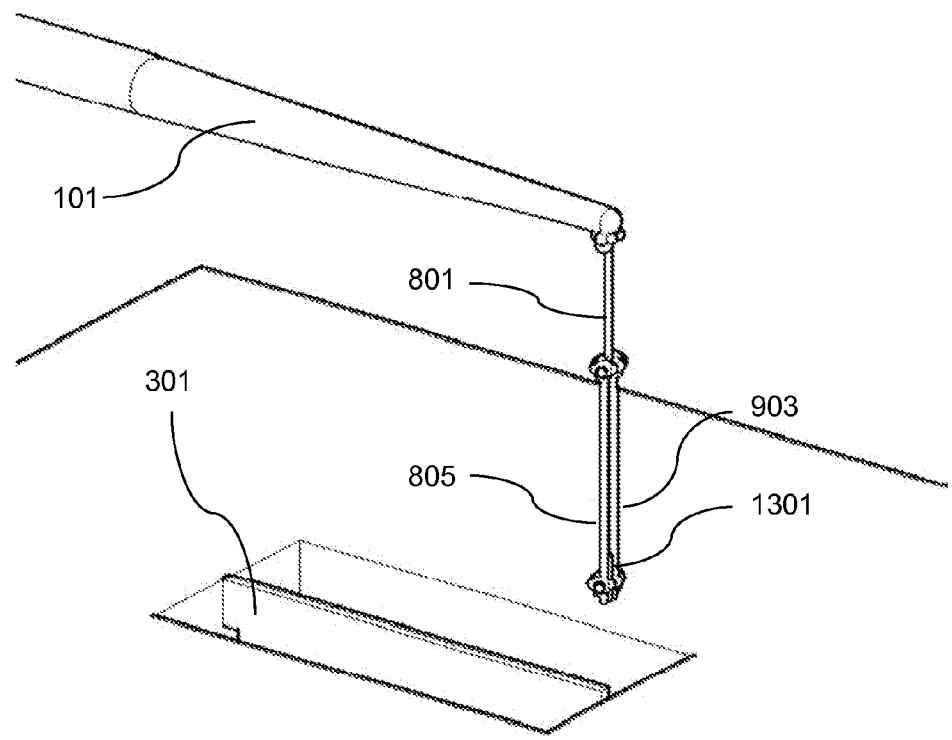
FIG. 14B shows the nanoloop moving towards the end of the specimen where there is a gap.
Figure 15A:
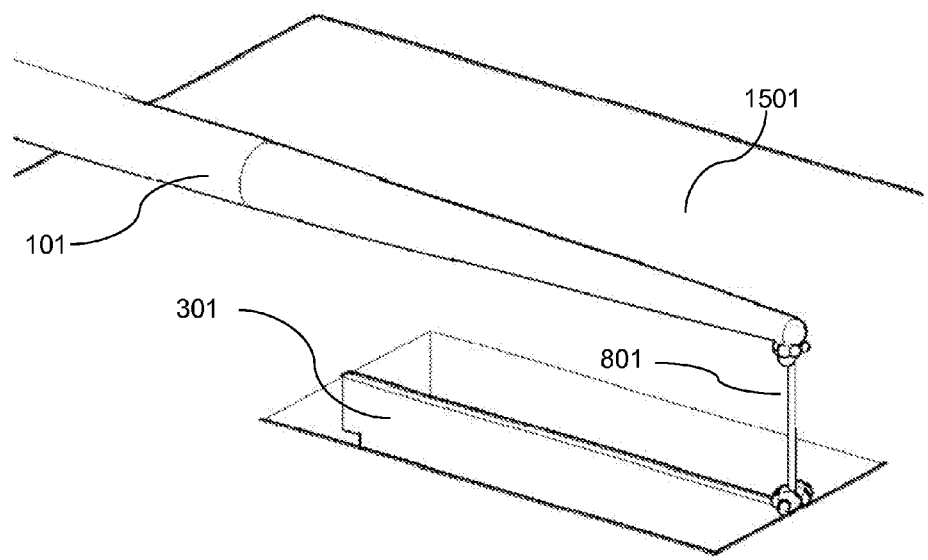
FIG. 15A shows the nanoloop entering the gap.
Figure 15B:
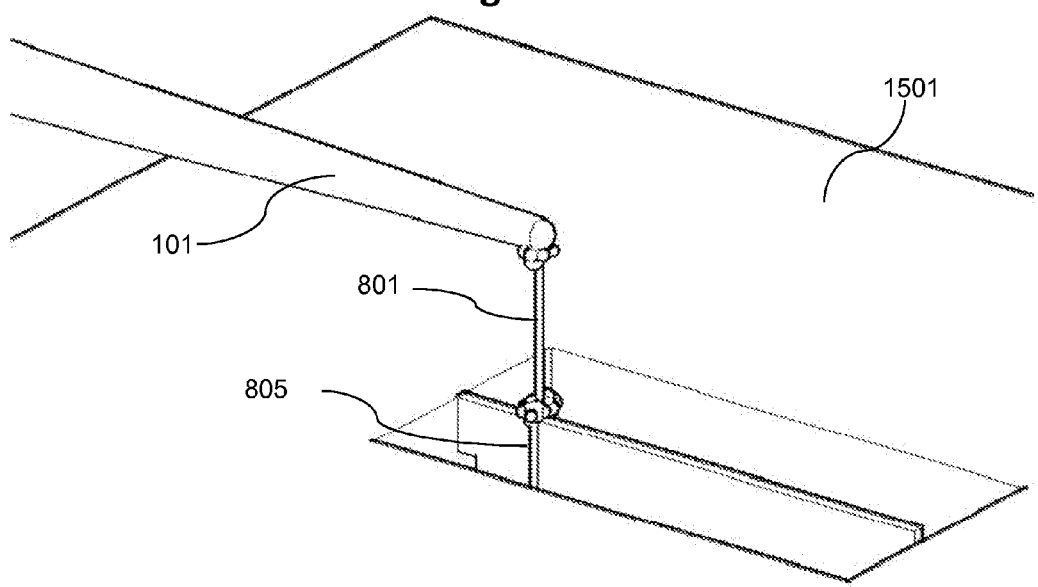
FIG. 15B shows the nanoloop sliding over the specimen.
Figure 16:
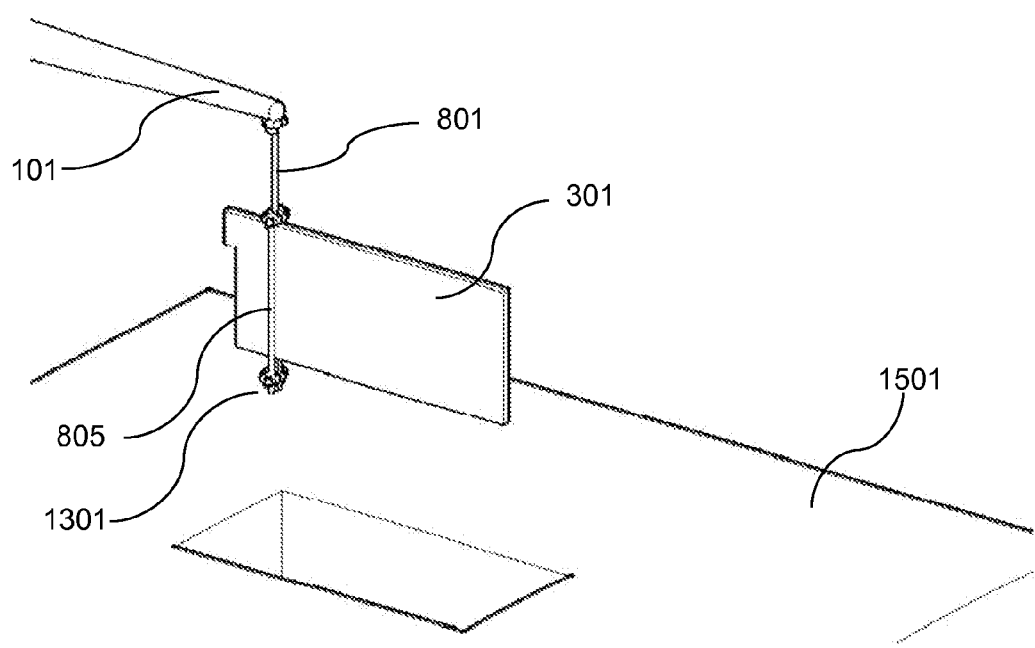

As shown in FIGS. 12 and 13, in yet another embodiment of the present invention, two or more nanoneedles as arms are bent and welded to each other at one end and also welded to a stem or otherwise a probe at the same end, while their concave sides are opposing each other to form a loop shape nano-tweezers. This embodiment which addresses the fabrication of the loop shape nano-tweezers comprises the steps of, (1) welding one needle (801) to the tungsten probe (101) to form a stem (FIG. 12a), (2) Welding a first branch (805) to first needles (801), (3) welding a second branch (903) to the first needle, (4) connecting and closing the freestanding end of the first (805) and second (903) branch to each other by welding (1301) and therefore forming a loop shape nano-tweezers (FIG. 13b). In this embodiment, there is a gap (903) that is larger than the size of the specimen (301), between the second (805) and third (903) branch in order for the specimen to easily slides in the loop as shown in FIG. 14-16. The specimen (301) slides between the arms of the loop shape nano-tweezers, and is held inside the closed loop only by the tips of the nanoneedles without a need for any kind of welding. The specimen (301) is then cut from the substrate (1501) and hold by the loop shape nano tweezers which is then moved away by the micromanipulator and as a result the specimen (301) is also moved away from substrate base (1501) as shown in FIG. 16.

One embodiment of the present invention is a method for modifying circuits even after they are coated/insulated by silicon oxides or similar materials. In this embodiment, the circuit is edited and/or redesigned by cutting through the insulated material and opening vias and connecting the vias by forming secondary connections using nanoneedles. The array substrate is used as supply for secondary connections and the nanomanipulator inside a control environment is used as mean for placing the secondary connections.

In one embodiment for modification of circuits, as a first step, vias, openings or other forms of cavity are created in the coating/insulating layer so that the conductors are exposed. After exposing the conductors by creating open cavities, the vias are filled with metal (e.g. tungsten) by ion beam deposition. In one embodiment, the deposited metal is at the same level or higher than the surface of the protective insulator. Then, appropriate exposed conductors (as determined by redesigning/modification needs) are connected using metal nanoneedles and micro manipulators to navigate.

One embodiment of a method of the present invention to connect two conductors in two vias comprises the following steps: (1) using a nanoneedle with a length equal to or larger than the distance between the two vias, a needle is attached to a tungsten probe that is in turn attached to a nanomanipulator arm, (2) the free end of the needle is brought into contact with the first conductor, welding the needle's free end to the conductor, (3) the probe is moved parallel to the substrate properly such that a mid-point of the needle or the probe-end of the needle touches a target conductor where it is welded to, and (4) finally the needle is cut off from the tungsten probe, leaving in place a nanowire connecting the first conductor to the second conductor.

In one embodiment, the free end of the nanoneedles is brought in contact with one of the metal deposited areas and welded to it (by ion beam metal deposition). Since these nanoneedles are flexible (very elastic), the needle are pushed slightly in such a way that some part of the needle (it can be either the very end, where it is welded to the micro-probes, or somewhere in the shaft of the needle) touches the second metal deposited area (previously deposited on the exposed electrode/conductor to fill the via) where it is subsequently welded to the metal contact followed by cutting the additional part of it. In yet another embodiment of the present invention, after a second point of the nanoneedle is welded to the target conductor and before cut-off, the micromanipulator can move again and aim towards connecting to a second target conductor. In other embodiments, this process is repeated as desired. In yet another embodiment, the cut-off actions are postponed to after all such inter-connections are performed, and then all cut-offs are performed in one or more shots as desired. In another embodiment, by choosing a nanoneedle with desired thickness, the electrical conductivity of the nanoneedle, therefore the connection between the two nodes can be adjusted as thicker nanoneedles are more conductive and thinner ones are less conductive.

Figure 17:
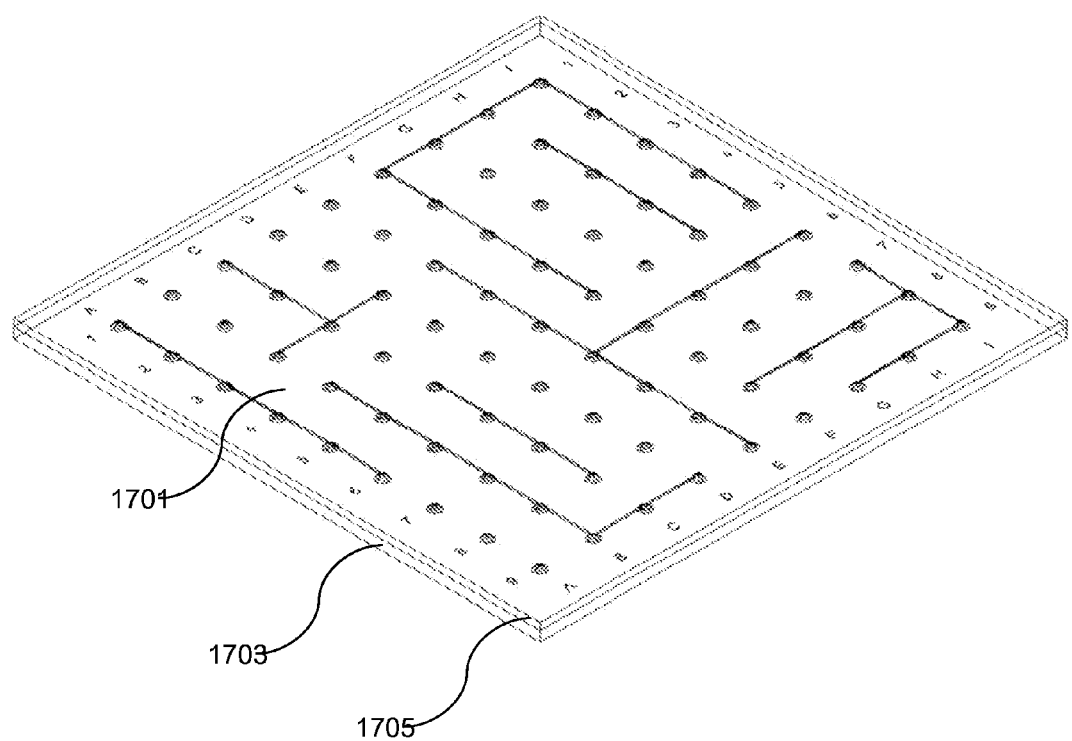
FIG. 17 shows a circuit that is edited using multiple nanoneedles for making additional contact between the multiple nodes.

An example of a general circuit (1701), with conductors (cylinders) connected to nodes/contacts (1707) is shown in FIG. 17. The circuit is printed onto a silicon chip (1703), and is then coated/insulated by a layer of silicon oxide (1705) to protect the circuit. In this drawing the silicon oxide layer is shown as a transparent layer on the surface of the circuit. The additional contact done by adding nanoneedles are shown by (1707).

Figure 18A:
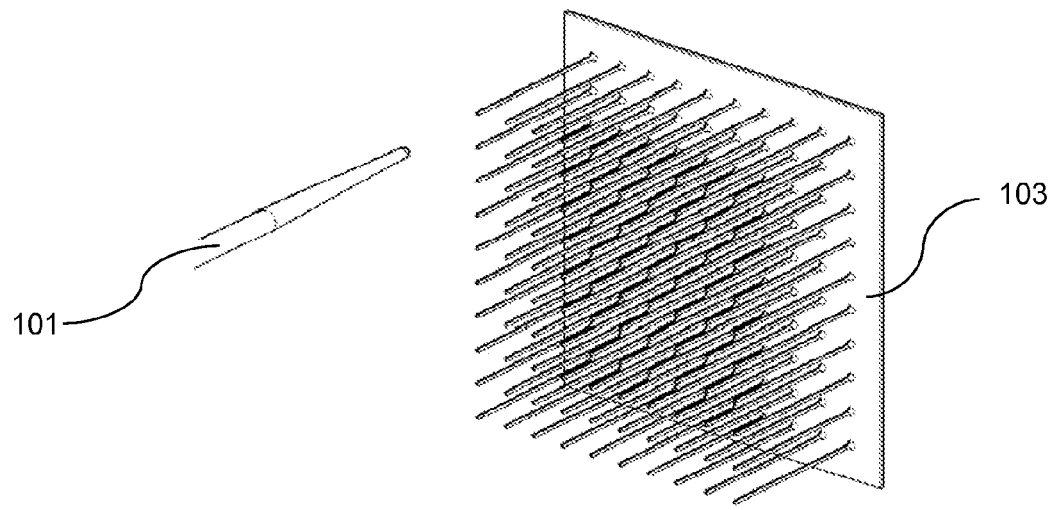
FIG. 18A shows schematic of a probe tip that is brought in contact with a needles array.
Figure 18B:
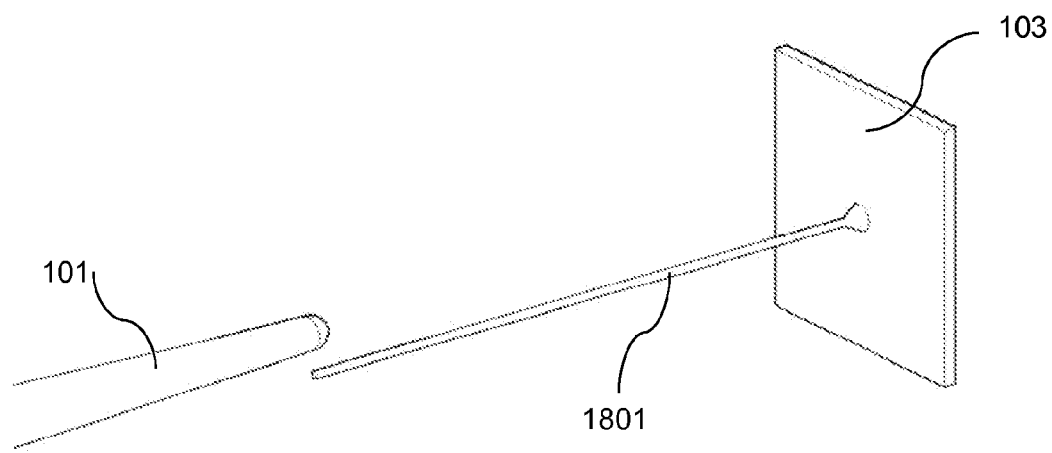
FIG. 18B shows the needles is welded in parallel to the probe tip.
Figure 18C:
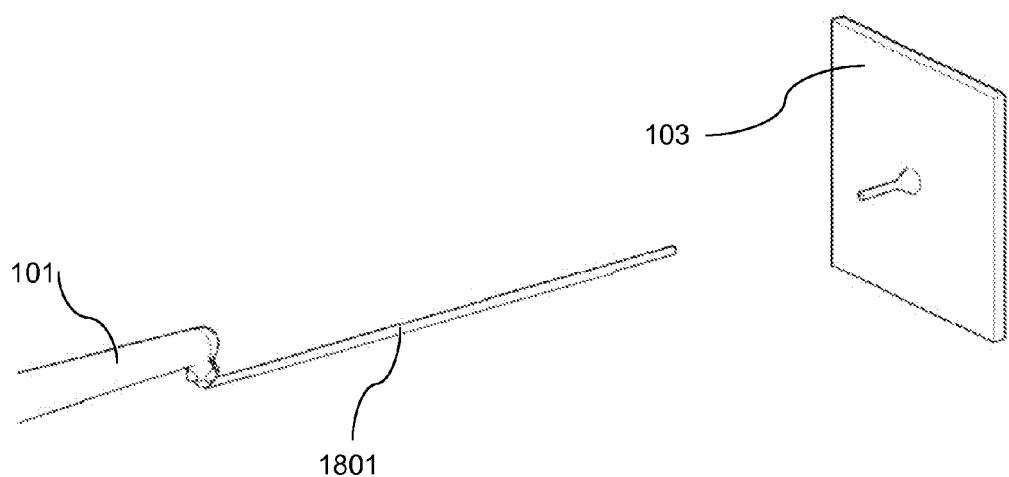
FIG. 18C shows the needles is cut from the array.
Figure 19:
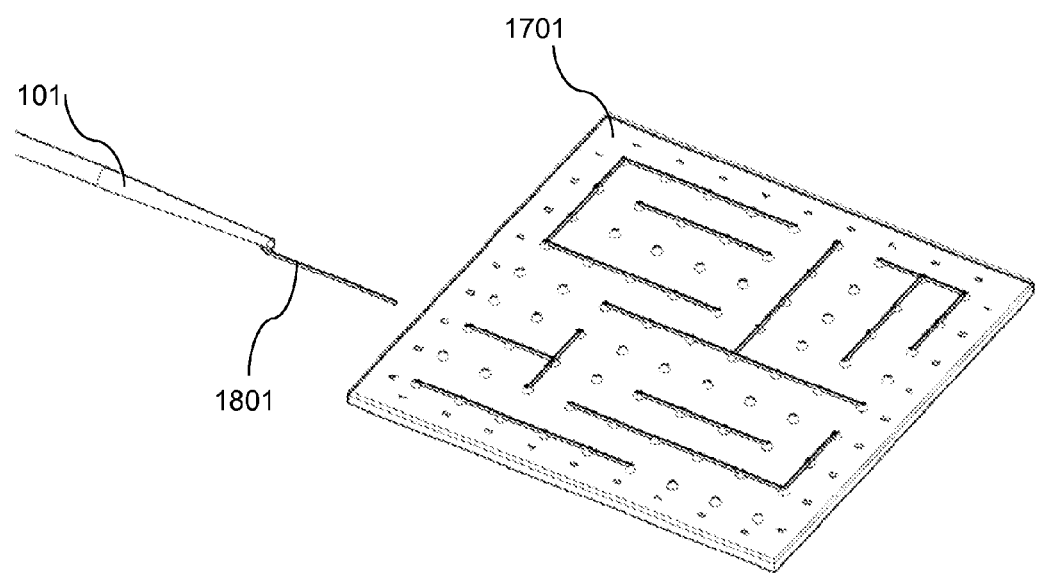
FIG. 19 shows a schematic of a needle that approaches to the circuit that is being edited.

One embodiment of the method for editing circuits (1701) presented in this invention comprises of cutting a hole through the silicon oxide layer above the nodes to be edited, exposing the contacts, and laying down a new conductive pathway between the nodes over the oxide/coating layer. As shown in FIGS. 18 and 19, one embodiment of a method of the present invention to connect two conductors in two vias comprises the following steps: (1) shown in FIG. 18 a-b, the tungsten wire/probe (101) is moved into position near the nanoneedle array (103), (2) shown in FIG. 18c a nanoneedle (1801) is welded to a tungsten probe (101) that is in turn attached to a nanomanipulator arm, and the nanoneedle (1801) is cut from the array substrate (103) to attach a nanoneedles (1801) to tungsten probe (103) in such a way that the length of the nanoneedle (1801) to be equal or longer than the distance between the two nodes (2001) that are going to be connected by the nanoneedle (1801).

As shown in FIG. 19, the nanoneedle (1801) is brought in proximity of the circuit to be edit (1701) using a nanomanipulator in a controlled environment. The nanoneedle (1801) is oriented to be aligned with/parallel to the surface of the oxide/coating later (FIG. 19b). The nanoneedle is positioned near the circuit to be edited. One embodiment of the method for editing circuits presented in this invention comprises of cutting a hole through the silicon oxide layer above the nodes to be edited, exposing the contacts, and laying down a new conductive pathway between the nodes over the oxide/coating layer. In this embodiment, the tungsten wire/probe is moved into position near the nanoneedle array. Then the tungsten wire is welded to the nanoneedle. The nanoneedle, now attached to the tungsten wire, is cut from the array and is positioned near the circuit to be edited. The nanoneedle is oriented to be aligned with/parallel to the surface of the oxide/coating later. The nanoneedle is positioned near the circuit to be edited.

Figure 20:
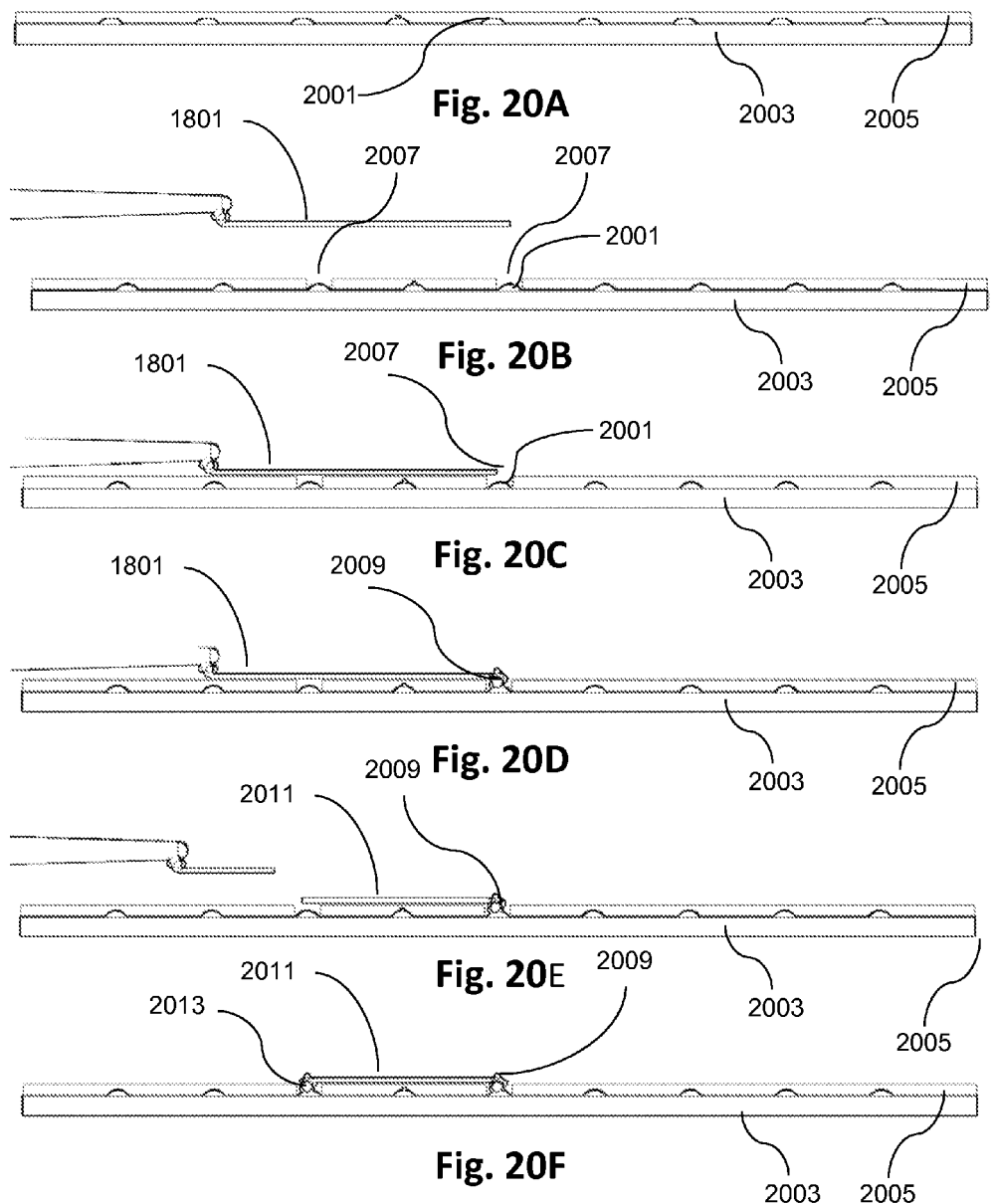
FIGS. 20A-E show a schematic of the sequences to edit the circuit by locating and welding the needle to a desire location between two opened vias.
FIG. 20F shows the welding of the nanoneedle at the desired location for second contact.
Figure 21:
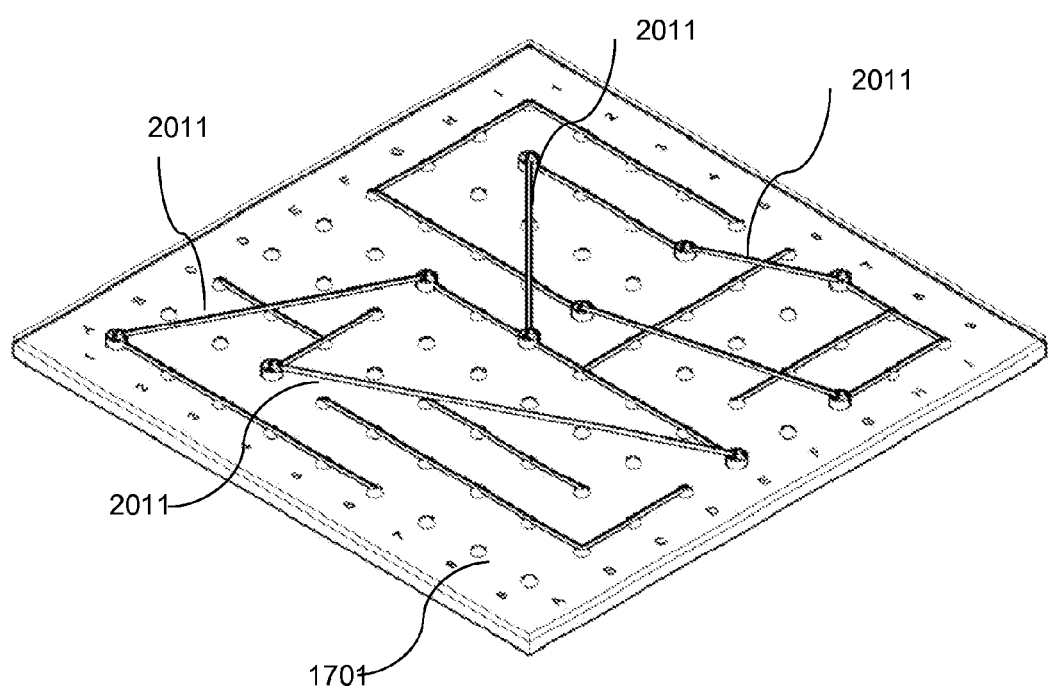
FIG. 21 shows a schematic of the circuit that has been further edited by adding additional needles to provide electrical contact between device nodes.

FIG. 20 shows the side view of the circuit as it is being edited by the method of this invention. As shown in FIG. 20a, the electrode nodes (2001) are under the silicon oxide layer (2005) and on the surface of the silicon layer (2003). As shown in FIG. 20b, two vias (2007) are cut in the silicon oxide layer to expose two nodes (2001) to be connected. Then, the nanoneedle (1801) is positioned over the exposed nodes (2001) to be connected. As shown in FIG. 20c, the nanoneedle (1801), positioned over the nodes, is brought down to the surface of the silicon oxide layer. As shown in FIG. 20d, the tip of the nanoneedle is welded (2009) to the first exposed node (2001). As shown in FIG. 20e, the nanoneedle, now connected to the first exposed node (2001), is cut just above the second exposed node (2007) to provide a nanoneedle bridge (2011) between the two nodes (2001). Figure FIG. 20f shows the nanoneedle bridge (2011) is welded (2013) to the second node, creating a conductive bridge (2015) between the two circuit nodes (2001). FIG. 21 shows a full view of the edited circuit (1701) after multiple nanoneedle bridges (2011) was added to the circuit.

Any variations of the above teachings are also intended to be covered by this patent application.

The invention claimed is:

1. A method of micromanipulation of a first specimen attached to a first base structure in a controlled space using a restorable tip on a microprobe, said method comprising, bonding said microprobe to a first freestanding nanoneedle in an array of freestanding nanoneedles, which stands out on a base substrate;

cutting off from said base substrate said first freestanding nanoneedle attached to said base structure, hence leaving in place said tip on said microprobe attached to a micromanipulator and a second nanoneedle segment attached to said base substrate;

bonding said tip to said first specimen;

cutting or otherwise releasing said first specimen from said first base structure;

moving said microprobe using said micromanipulator to displace said first specimen to a desired location; and cutting said tip to release said first specimen in said desired location.

2. The method of claim 1 further comprising restoring said tip when shortened by:

bonding said tip to a second freestanding nanoneedle on said array of freestanding nanoneedles; and cutting off from said base structure said second freestanding nanoneedle.

3. The method of claim 1 further comprising creation of a new tip by:

bonding said microprobe to a second freestanding nanoneedle on said array of freestanding nanoneedles; and cutting off from said base structure said second freestanding nanoneedle hence creating said new tip and restoring said microprobe.

* * * * *